US00PP20885P3

(12) United States Plant Patent
Young et al.

(10) Patent No.: US PP20,885 P3
(45) Date of Patent: Mar. 23, 2010

(54) PINEAPPLE PLANT NAMED 'DOLE-14'

(50) Latin Name: *Ananas comosus*
Varietal Denomination: Dole-14

(75) Inventors: Roberto Young, Westlake Village, CA (US); Jorge Gonzales, San José (CR)

(73) Assignee: Dole Food Company, Inc., Westlake Village, CA (US)

( * ) Notice: Subject to any disclaimer, the term of this patent is extended or adjusted under 35 U.S.C. 154(b) by 0 days.

(21) Appl. No.: 12/215,534

(22) Filed: Jun. 26, 2008

(65) Prior Publication Data

US 2009/0328260 P1 Dec. 31, 2009

(51) Int. Cl.
*A01H 5/00* (2006.01)

(52) U.S. Cl. ..... Plt./156
(58) Field of Classification Search ..... Plt./156
See application file for complete search history.

*Primary Examiner*—Kent L Bell
(74) *Attorney, Agent, or Firm*—Morrison & Foerster LLP

(57) ABSTRACT

A new pineapple (*Ananas comosus*) variety of the Bromeliaceae family was developed from a cross made by Dole between the commercial variety 'MG-03' and 'P-1972', a patented clone, and has been designated 'Dole-14'. This new variety differs from its progenitors in having higher carotenoid content, medium acidity, low fiber content, improved aroma, distinct fruit flavor and flesh colors, and a conical to cylinder shaped fruit with a long conical crown. It also shows high tolerance to NDF and less susceptibility to shell cracking. The plant is characterized by long spineless leaves with piping, that are pale to grayish green in color. When unripe, fruit shell is pale green turning to uniform yellow color when ripe, and the flesh develops a deep golden color at maturity.

3 Drawing Sheets

Latin name: *Ananas comosus.*
Variety denomination: 'DOLE-14'.

The invention refers to a new plant variety of pineapple (*Ananas comosus*) family Bromeliaceae, subclass of Monocotyledons, and named 'Dole-14'. The fruit has a distinctly unique aroma and exquisite sweet flavor, higher carotenoid content which gives a deep golden color to the pulp, which also has both medium acidity and lower fiber content, compared to its progenitors. This new variety is tolerant to natural occurrence of flowering (NDF).

BACKGROUND OF THE INVENTION

Pineapple is a popular fruit worldwide. There is a continued need for improved varieties, particularly those varieties with a higher carotenoid content and increased sweetness.

SUMMARY OF THE INVENTION

The new pineapple (*Ananas comosus*) variety, 'Dole-14', differs from its parents in having higher carotenoid content reflected in a deeper golden yellow flesh, improved aroma, distinct sweet flavor, lower fiber content of the pulp, and a conical to cylinder shaped fruit with a conical crown. It also shows higher tolerance to both NDF and shell cracking when compared to its female and male parent respectively. The plant is characterized by long, spineless leaves with piping that are pale to grayish green in color. Fruit shell is thin and the flesh has medium acidity as compared to its progenitors.

BRIEF DESCRIPTION OF THE DRAWINGS

The accompanying photographs depict the new variety 'Dole-14' and its progenitors: 'Mayan Gold-03' and 'P-1972'.

DETAILED DESCRIPTION OF THE INVENTION

Figure 1:
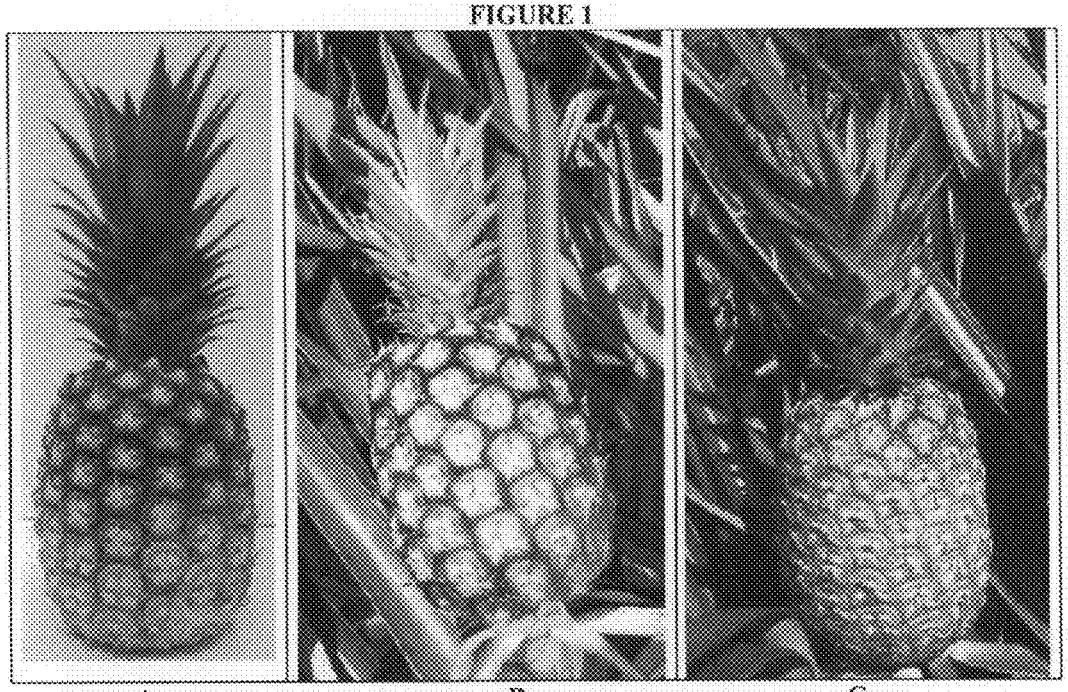
FIG. 1A shows fruit of the female parent 'Mayan Gold-03'.
FIG. 1B shows fruit of 'Dole-14'.
FIG. 1C shows fruit of the male parent 'P-1972'.
Figure 2:
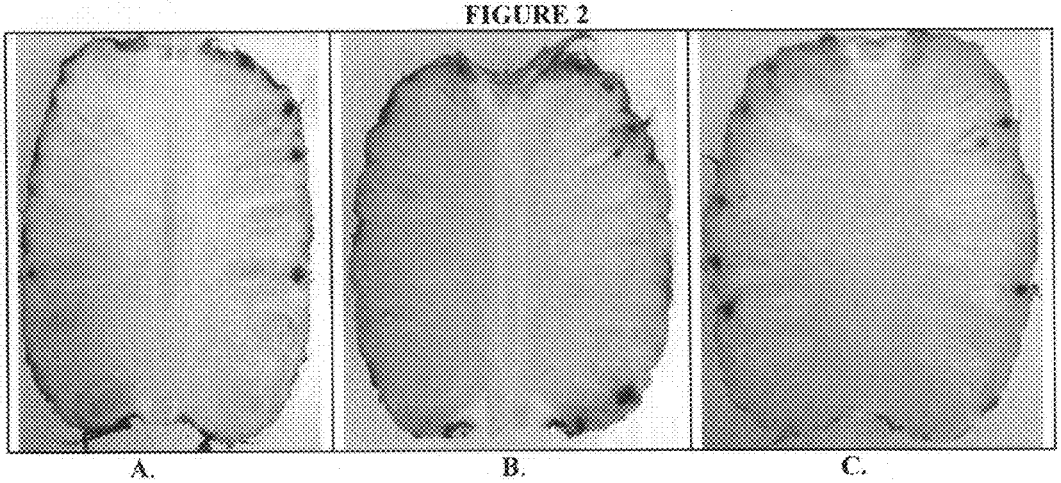
FIG. 2A shows fruit pulp of female parent 'Mayan Gold-03'.
FIG. 2B shows fruit pulp of 'Dole-14'.
FIG. 2C shows fruit pulp of male parent 'P-1972'.
Figure 3:
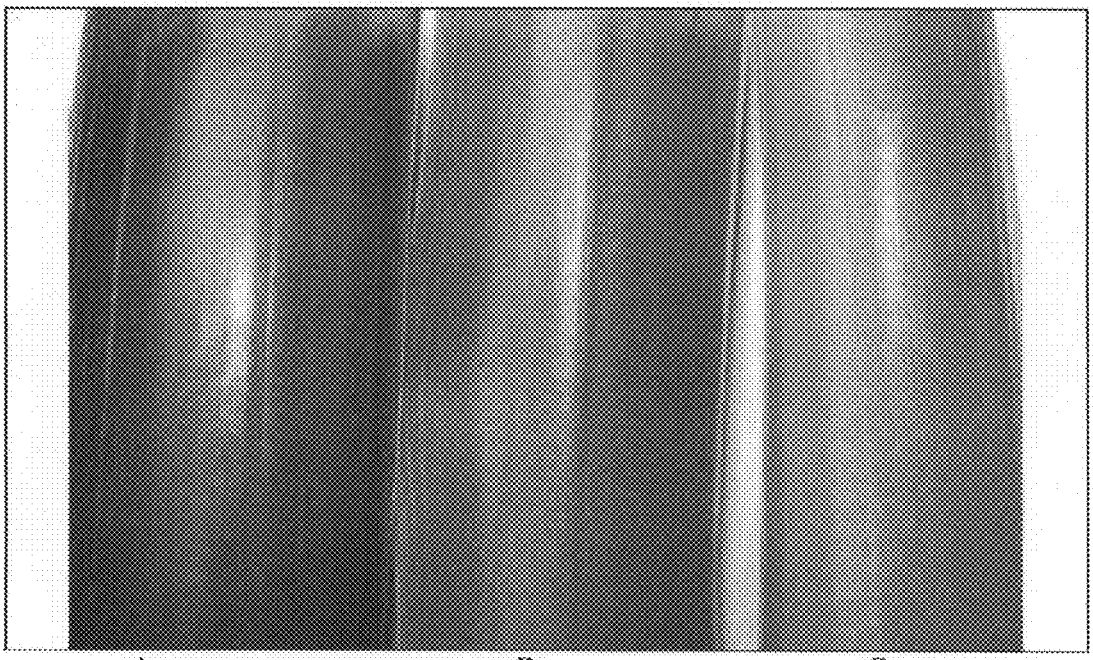
FIG. 3A shows a 'Mayan Gold-03' leaf.
FIG. 3B shows a 'Dole-14' leaf.
FIG. 3C shows a 'P-1972' leaf.
Figure 4:
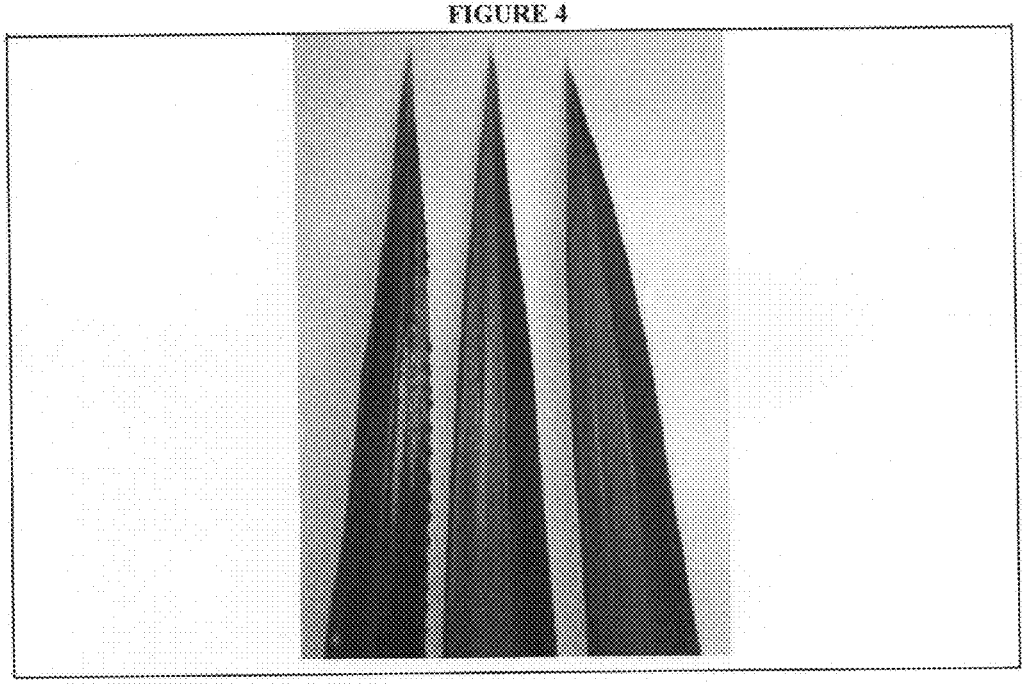
FIG. 4A shows a leaf tip of 'Mayan Gold-03'.
FIG. 4B shows a leaf tip of 'Dole-14'.
FIG. 4C shows a leaf tip of 'P-1972'.
Figure 5:
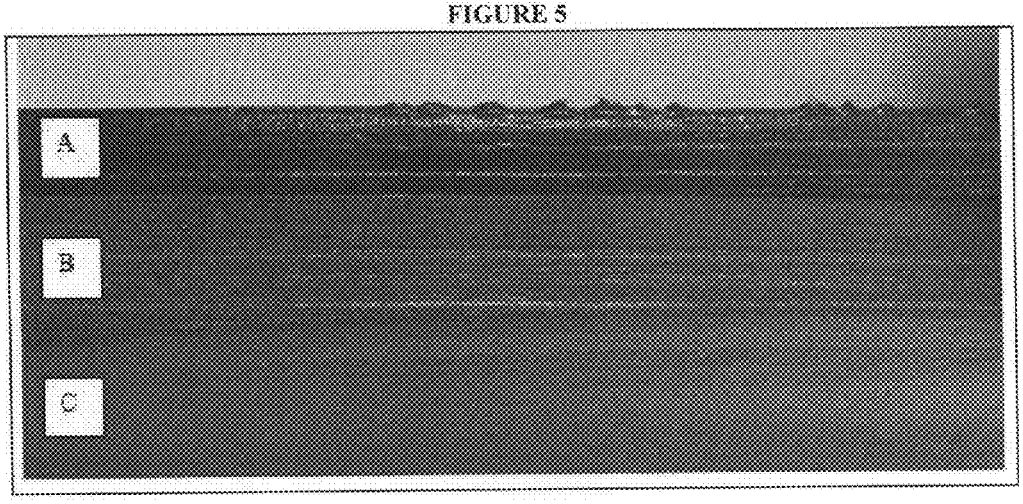
FIG. 5A shows a leaf margin of 'Mayan Gold-03'.
FIG. 5B shows a leaf margin of 'Dole-14'.
FIG. 5C shows a leaf margin of 'P-1972'.

'Dole-14' was originally selected as an individual plant within a segregating population produced from seed from a cross carried out in 1997 between 'Mayan Gold 03' and 'P-1972', and named '9700MC-03/02-003'. Testing and selection of three consecutive asexual generations took place from 2002 through 2007, in Honduras - Central America.

Parental Description: The variety 'Mayan Gold 03' or 'MG-03' was derived from crossing Pineapple Research Institute of Hawaii hybrid clones 58-1184 and 59-443. 'Mayan Gold 03', also known as 'Tropical Gold', is a popular commercial variety appreciated for its yellow and golden yellow shell and pulp color when ripen respectively. Regularly, leaf margins in 'Mayan Gold 03' are devoid of spines; however spines may be present and their abundance and distribution may vary depending on the environmental conditions. Fruit is mostly conical to cylindrical-sharp taper in shape, with a long conical and attractive crown, and weighing approximately 1.9 Kg. The flesh in 'Mayan Gold 03' is smooth in texture, with small to intermediate amount of fiber, and with high content of vitamin C. Brix/Acid ratio ranges from 28°–35° , favoring a pleasant and mostly sweet flavor. 'Mayan Gold 03' is resistant to both FCR (Fruitlet Core Rot) caused by *Fusarium moniliforme*, and Blackheart, but it is highly susceptible to root rot caused by *Phytophtora cinnamomi*.

The parental lines from which 'P-1972' was derived, included two clones previously developed by the Pineapple Research Institute, namely '64-337' and '59-443'. 'P-1972' has unique characteristics such as distinctive fruit aroma and flavor, and deep yellow color of both shell and flesh due to high carotenoid content. The plant is characterized by long spineless leaves with piping, pale to grayish green in color, with veins protruding from the leaf surface. The plant has a uniform cylindrical and symmetrical fruit with a smooth and thin shell and flat fruitlets or eyes. Fruit is borne on a short peduncle and the crown is long and conical, with an average weight of 1.5 Kg. Incidence of FCR and marbling is low in P-1972, and it shows high tolerance to NDF. During the dry season when temperatures are high, the fruit may develop the shell cracking defect. 'P-1972' is a patented variety (U.S. Plant Pat. No. 16,396 P3).

This breeding effort aimed to produce a fresh fruit variety with pleasant and distinct aroma and flavor, tolerant to both premature flowering and shell cracking, and with high shell color and high carotenoid content in the pulp.

The development of the new variety started in the North coast of Honduras. A segregating population was produced by cross-pollinating flowers of 'MG-03' with pollen taken from plants of the variety 'P-1972' in 1997. The first plant selection was practiced in year 2000, and was named '9700MC- 03/02-003' later named 'Dole-14'. Genetic stability of this selection was evaluated during three consecutive asexual generations which took place from 2002 through 2007.

Different methods of asexual propagation were used for variety multiplication, i.e. stem cuttings, slips, suckers, gouging of fruit crowns, and tissue culture derived plants.

'Dole-14' shows unique characteristics such as distinctive fruit aroma and flavor, a deep golden colored fruit pulp due to a high carotenoid content, and a conical shaped fruit with a conical crown. Conducive NDF conditions occurring during three consecutive winter seasons revealed that the new pineapple hybrid 'Dole-14' is highly tolerant to natural flowering. This new hybrid has also shown no susceptibility to shell cracking during the dry and hot season in the North Coast of Honduras. The new variety is stable and has reproduced true to type in three successive generations of asexual reproduction.

BOTANICAL DESCRIPTION OF THE PLANT

The following is a description of the new plant variety based on observations made prior to forcing in December of 2006 and October of 2007, and at harvesting in May of 2007 and February of 2008, grown in the North Coast of Honduras (15 degrees 44 minutes latitude north, and 86 degrees 53 minutes longitude west). The average temperature in the North Coast Honduras is 26° C., with 3,542-mm of annual average precipitation. The Munsell Color Chart was used for all color designations ("Munsell Book of Color" Gretag Macneth LLC, 617 Little Britain Road, New Windsor, New York 12553-6148).

Name: *Ananas comosus* (L.) Merr. Var. 'Dole-14', family Bromeliaceae, subclass Monocotyledons.

Parentage:

*I. Seed parent.*—Commercial variety 'Mayan Gold 03'.

*II. Pollen parent.*—Patented variety 'P-1972'.

Classification:

*I. Botanic.*—Family: Bromeliaceae family. Subfamily: Bromeliacidae. Genus: *Ananas*. Species: *comosus*. Cultivars: 'Mayan Gold 03'×'P-1972'.

*II. Commercial.*—Bromeliad fruit plant.

General form: During the vegetative stage, 'Dole-14' has an intermediate foliage attitude and consists of a compact rosette of overlapping sessile leaves arising from a central stem and surrounding a composite inflorescence prior anthesis. Production of offshoots (suckers, hapas and slips) is very limited, but depending on season slips may vary from 0 to 2.0±2.4 per plant. Plant height may vary depending on growing conditions from 120±9.4 to 136±9.4 cm, without fruit. Mean stem diameter ranges from 6.0±0.3 to 6.7±0.6 cm, measured at the base at forcing time in a 2.7 Kg plant.

Stems: Stem is upright, sheathed by overlapping leaves arranged in acropetal fashion, forming a heart shape stem. The stem color is whitish (5Y 8/2 to 8/4).

Leaves:

*I. General.*—leaves are sessile, lanceolate in form, elongated and succulent, with acuminate apex shape, and forming a rosette with a 5/13 phyllotaxy. Depending on growing conditions, the number of leaves per plant may vary from 41±4.6 to 57±5.9. The breakage resistance of the leaf is medium, and foliage attitude is open (Descriptors for Pineapple, IBPGR, Rome 1991). Trichomes are present in the abaxial side of the leaves.

*II. Color.*—The color of the upper and lower surfaces of the D leaf is green (5GY 5/6 to 5/10) and light green (5GY (7/6 to 7/10)) respectively.

*III. Margins.*—The leaves are completely spineless showing the presence of piping, which is a narrow silvery (2.5GY 8/2) stripe extended over the adaxial surface along the leaf edge. Margin color is green but slightly darker than the middle section (5GY 5/8 to 5/10). Longest leaf thickness is on average 2.2±0.3 mm at middle section.

*IV. Leaf size.*—Depending on growing conditions, measurements taken on D leaf may vary from 110±7.8 to 120.4±7 cm in length, and 5.9±0.4 to 6.3±0.6 cm in width at middle section.

Inflorescence:

*I. General.*—Pineapple inflorescence of composite flower, with self-incompatible individual bi-sexual flowers containing three sepals (10.5±0.4 mm in length), six stamens (15.6±0.8 mm in length), three stigmas (1.4±0.4 mm wide), and three carpels (5.8±0.8 mm in width). The inflorescence is borne in a long conical peduncle (21.5±3.7 cm in length, and 2.6±0.3 cm in diameter at middle section). The number of days to flowering after forcing is as follows: 47 days to the presence of floral bud, and 59 days to first flower. The inflorescence length mid flower stage is 10.9+/−0.5 cm. The inflorescence diameter mid flower stage is 6.3+/−0.5 cm.

*II.*—The penduncle bract has a lanceolate form. The average number of peduncle bracts is 5+/−1.3, with a longest bract length of 18.7+/−6.2 cm. The floral bract, which covers ⅓ of the fruitlet, is of aristate apex and truncate base. The floral bract width is 23–27 mm and has a smooth edge. The floral bract color at the abaxial side of the tip is brownish (5Y 7/10, 6/8, 5/6), and greenish at the base (5GY 7/8–6/18).

*III.*—Petals are smooth with an oblong shape and a closed orientation. Petals are 20.8±1.0 mm in length, and 6.5±0.6 mm in width. The petal number is 3. The apex is subacute and the base is truncate. Petal color is white at the base and deep purple at the tip (5RP 3/4 to 3/8).

*IV.*—The sepals are smooth with an orbicular shape and are 10.5+/−0.4 mm in length. The apex is obtuse. The coloration of both surfaces is greenish-green (5GY 5/10 to 6/10).

Fruit:

*I. Fruit shape.*—The fruit is cone to cylinder shaped, with a diameter of 13.2±0.6 cm at middle part. The shell is smooth and thin (3.3±0.5 mm). The number of fruitlets is 101.5±10.2, averaging 7.6±1.1 spirals, and 13.4±1.2 fruitlets in the longest spiral. The coloration of the fruitlet is yellow (2.5Y (8/8 to 8/10) & 7.5YR 7/10).

*II.*—Fruit and crown average heights are 15.1±1.0 and 15.0±3.7 cm respectively for a fruit/crown ratio of 1.0. Mean fruit weight is 1.7±0.2 Kg.

*III. Crown characteristics.*—The crown is conical in shape, weighing 136.7±28.1 g. Leaf color is green (5GY 4/6, 4/8, 5/6). Leaves are spineless and smooth, with piping in leaf margins.

*IV. Flesh and juice characteristics (grade* 5).—The flesh is compact, dense, smooth texture with small amount of fibers and distinct aroma. Core diameter is 2.4±0.2 cm. Flesh color is orange-yellow to golden yellow (2.5Y 8/8, 8/10), and with acceptable translucency appearance. Table 1 compares fruit quality values for 'Dole-14', its progenitors, and other known pineapple varieties or clones.

*V. Peduncle.*—Fruit develops from the apical meristem of the plant on a peduncle, usually 21.5±3.7 cm in length, and 2.6±0.3 cm in diameter. Approximately, 5.0±1.3 bracts can be growing in a peduncle. The average length of the longest bract is 18.7±6.2 cm.

*VI.*—Table 2 compares the tolerance of 'Dole-14' and known varieties to certain pests, diseases and other disorders.

TABLE 1

Comparison of internal fruit quality characteristics at maturity grade 3, between 'Dole-14' and other known varieties/clones, under the North Coast of Honduras conditions during 2007 growing season.

| Pineapple Variety | Brix | | Acid % | Brix/ Acid Ratio | Caro-tenoids (ppm) | Ascorbic Acid (mg/100 ml) |
|---|---|---|---|---|---|---|
| 'Dole-14' | Average | 17.1° | 0.57 | 31 | 10 | 43 |
| | Stdev. ± | 1.6 | 0.1 | 6 | 3 | 10 |

TABLE 1-continued

Comparison of internal fruit quality characteristics at maturity grade 3, between 'Dole-14' and other known varieties/clones, under the North Coast of Honduras conditions during 2007 growing season.

| Pineapple Variety | Brix | | Acid % | Brix/ Acid Ratio | Caro-tenoids (ppm) | Ascorbic Acid (mg/100 ml) |
|---|---|---|---|---|---|---|
| 'Tropical Gold' | Average | 14.6° | 0.69 | 22 | 7 | 44 |
| | Stdev. ± | 1.4 | 0.2 | 6 | 3 | 15 |
| 'P-1972' | Average | 14.3° | 0.57 | 29 | 9 | 29 |
| | Stdev. ± | 2.1 | 0.2 | 14 | 3 | 9 |
| 'MD-2' | Average | 14.4° | 0.62 | 24 | 8 | 55 |
| | Stdev. ± | 0.8 | 0.2 | 6 | 4 | 18 |
| 'Josapine' | Average | 17.6° | 0.68 | 26 | 9 | 23 |
| | Stdev. ± | 1.7 | 0.1 | 1 | 3 | 4 |
| 'Tainung-9' | Average | 18.8° | 0.53 | 36 | 9 | 16 |
| | Stdev. ± | 2.0 | 0.1 | 5 | 4 | 7 |
| 'Taboga' | Average | 15.4° | 0.65 | 24 | 1 | 28 |
| | Stdev. ± | 1.3 | 0.1 | 2 | 0 | 1 |
| 'Red Spanish' | Average | 14.5° | 0.74 | 22 | 2 | 5 |
| | Stdev. ± | 0.6 | 0.3 | 9 | 0.4 | 1 |
| 'McGregor' | Average | 13.4° | 1.15 | 12 | 5 | 17 |
| | Stdev. ± | 1.1 | 0.02 | 1 | 0.4 | 4 |

TABLE 2

Tolerance comparisons of 'Dole-14' and known varieties to certain pests, diseases, and other disorders when grown under the North Coast of Honduras conditions.

| Condition | 'Dole-14' | 'Tropical Gold' | 'P-1972' | 'Mayan Gold 01' | 'Cham-paka' |
|---|---|---|---|---|---|
| Phytophtora | moderate | low | moderate | high | high |
| Erwinia | moderate | low | moderate | high | high |
| Army worm | low | none | low | low | low |
| Mealybug (*pseudococcus* ]brevipes) | low | none | low | low | low |
| Natural Flowering | high | low | high | moderate | moder-ate |
| Translucency | high | low | moderate | moderate | high |
| Fruitlet Core Rot | high | high | high | high | moder-ate |
| Internal Brown Spot | high | high | high | high | low |
| Fruit Cracking | high | high | moderate | high | high |
| Open Eye | high | high | moderate | high | high |
| Crown Defects | high | moderate | high | low | low |

What we claim:

1. A new and distinct variety of pineapple plant designated 'Dole-14' substantially, as shown and described herein.

* * * * *

A. B. C.

A. B. C.

A. B. C.

A. B. C.